United States Patent [19]

Thatcher et al.

[11] 4,038,321

[45] July 26, 1977

[54] PROCESS FOR PRODUCTION OF UNSYMMETRICAL DIMETHYLHYDRAZINE BY NITROSATION OF DIMETHYLAMINE AND HYDROGENATION OF THE NITROSO DIMETHYLAMINE TO THE DISTILLATION OF UNSYMMETRICAL DIMETHYLHYDRAZINE

[75] Inventors: Donald N. Thatcher, Hollister; Yoshiyuki Arikawa, Gilroy, both of Calif.

[73] Assignee: Teledyne McCormick Selph, Hollister, Calif.

[21] Appl. No.: 648,226

[22] Filed: Jan. 12, 1976

[51] Int. Cl.$^2$ .................. C07C 109/02; C07C 111/00
[52] U.S. Cl. .......................... 260/583 B; 260/583 CC; 260/583 N
[58] Field of Search ................... 260/583 CC, 583 B

[56] References Cited

U.S. PATENT DOCUMENTS

| 2,754,329 | 7/1956 | Bashford | 260/583 CC |
|---|---|---|---|
| 2,802,031 | 8/1957 | Horvitz | 260/583 CC |
| 2,960,536 | 11/1960 | Getz | 260/583 CC |
| 3,098,017 | 7/1963 | Walter et al. | 260/583 B |
| 3,129,263 | 4/1964 | Feldman et al. | 260/583 CC |
| 3,153,094 | 10/1964 | Reilly | 260/576 |
| 3,164,535 | 1/1965 | Diamond et al. | 260/583 CC |
| 3,454,361 | 7/1969 | Huber et al. | 260/583 B |

FOREIGN PATENT DOCUMENTS

| 644,820 | 7/1962 | Canada | 260/583 CC |
|---|---|---|---|
| 654,797 | 12/1962 | Canada | 260/583 CC |

OTHER PUBLICATIONS

"Sidgwick's Organic Chemistry of Nitrogen," 3rd Edition, pp. 506, 592, 593, 609, 610 and 611, (1966).

*Primary Examiner*—Daniel E. Wyman
*Assistant Examiner*—John J. Doll
*Attorney, Agent, or Firm*—David H. Semmes; Warren E. Olsen

[57] ABSTRACT

A process for production of unsymmetrical dimethylhydrazine from nitroso dimethylamine that is characterized as a completely closed system with respect to positive prevention of environmental contamination by waste nitrosodimethylamine. This process further provides a novel extraction step which also produces, as a solid by-product, potassium nitrate without nitrosodimethylamine contamination.

13 Claims, 7 Drawing Figures

PROCESS FOR PRODUCTION OF UNSYMMETRICAL DIMETHYLHYDRAZINE BY NITROSATION OF DIMETHYLAMINE AND HYDROGENATION OF THE NITROSO DIMETHYLAMINE TO THE DISTILLATION OF UNSYMMETRICAL DIMETHYLHYDRAZINE

BACKGROUND OF THE INVENTION:

The process according to the instant invention is for the manufacture of Unsymmetrical Dimethylhydrazine (UDMH) which is useful for fuels, intermediates for chemical syntheses and the like. N-nitrosodimethylamine (NDMA) has been identified by Department of Labor safety orders as a cancer suspect agent, i,e., a carcinogen. This material is an intermediate compound of the instant process for manufacture of unsymmetrical dimethylhydrazine (UDMH).

Because NDMA is an indicated carcinogen, a significant object of the invention is to employ closed-loop processing with recycling of all waste streams. Additionally the instant invention teaches a positive treatment of all liquid, vapor and solid sidestreams to prevent NDMA exposure to chemical operators or to the environment.

For example, the Federal Safety Order definition of acceptable NDMA concentration is 1% by weight or volume. According to the method of the instant invention all NDMA would be destroyed in each and every waste stream.

Of significance is the fact that there are three ordinary outlets from the instant process and these lead to either a thermal destructor or a rotary flaker and the third one is the final product, UDMH. All vapor and liquid waste is thoroughly treated to destroy NDMA in the thermal destructor. One solid by-product, potassium nitrate salt, is similarly treated in a high temperature melt pot of a rotary flaker destroying all final traces of NDMA. UDMH, the final product of this process also contains only minute quantities of NDMA.

SUMMARY OF THE INVENTION

The instant process teaches the synthesis of unsymmetrical dimethylhydrazine (UDMH) from dimethylamine (DMA), with a nitrosation of DMA to N-nitrosodimethylamine (NDMA) and the catalytic hydrogenation of NDMA to UDMH. The theoretical equations can be written as follows:

$$2(CH_3)_2NH + 2N_2O_4 + K_2CO_3 \rightarrow 2(CH_3)_2NNO + KNO_3 + H_2O + CO_2$$

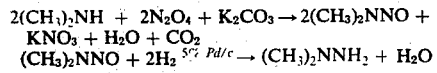

Side reactions that occur which lower the yield of UDMH include cleavage of the DMA in the nitrosation reaction leading to the formation of methanol, formaldehyde and other cleavage products. In the hydrogenation, additional hydrogenation of UDMH can occur with the resultant formation of DMA concurrently with the formation of ammonia ($NH_3$). In addition to yield losses in the synthesis steps of this reaction, the isolation of 98% UDMH by distillation involves some additional process losses for the concentration.

The instant process for UDMH has been carried out with the nitrosation, hydrogenation and distillation as consecutive reactions in the same reactor. It has the advantage of having a closed system without isolation of intermediate products. Several disadvantages were evident. First, hydrogenation in the presence of potassium nitrate ($KNO_3$) led to the reduction of the nitrate ion to Ammonia ($NH_3$). The removal of $NH_3$ imposes additional problems in the distillation stage. Second, the concentration of UDMH for distillation was limited by the presence of salt from the nitrosation process, thus, placing additional requirements on the distillation step.

While the instant invention teaches a nitrosation of DMA to NDMA as an initial step, as such this step is a well-known manner of forming an intermediate NDMA product. For example, U.S. Pat. No. 3,153,094 to Reilly teaches one type of nitrosation using nitric oxide (NO) and DMA. It should be noted, however, that the instant nitrosation uses dinitrogen tetroxide ($N_2O_4$) and as such this reactant illustrates that even this step is a departure from known nitrosation technique.

From initial laboratory tests, it has been shown that with this nitrosation DMA could be converted to NDMA in yields approaching 100%. The most critical feature is the temperature of reaction. A yield of 95% was assumed for process flow sheets.

However, hydrogenation of an aqueous solution directly from the nitrosation would lead to the reduction of $KNO_3$ to $NH_3$. Therefore, one major aspect of this process is the isolation of the $KNO_3$ from NDMA before the hydrogenation step by an extraction. Any method may be used for the isolation of $KNO_3$ from NDMA and the preferred embodiment illustrates the process for a 20–30% aqueous NDMA solution for the hydrogenation step.

Two methods for isolating NDMA from the $KNO_3$ salt solution were contemplated:
1. Vacuum crystallization of $KNO_3$
2. Extraction of NDMA with methylene chloride Following are some advantages and disadvantages of the above two processes:

| Crystallizer | Extractor |
|---|---|
| Advantages | |
| 1) safe operation | 1) simple and safe |
| 2) known process | 2) comparatively low cost |
| 3) closed system | 3) continuous and closed system |
| Disadvantages | |
| 1) high capital cost | 1) dilution of salt solution necessary before extraction |
| 2) problem of handling salt after separation | 2) additional ingredient (methylene chloride) required |
| 3) dilute NDMA solution produced | |

Based on the considerations that the extraction process is preferred as simpler; being a continuous closed system process that results in concentration NDMA solutions for hydrogenation, the extraction process is illustrated herein.

For the important extraction step according to the instant process a dilute solution from the dilution tank may be fed to the extracting column at its base. Recovered methylene chloride may be fed in at the top by a methylene chloride feed pump. The flow rates of NDMA-salt solution and methylene chloride are adjusted to the desired ratios. A specified agitation speed stroke and length are set at the start of feeds input.

The methylene chloride layer containing NDMA is withdrawn at the bottom and fed to a flash evaporator via storage tank and pump. The aqueous layer containing nitrate and unrecovered NDMA is withdrawn at the top of the column (just above the methylene chloride input) for further processing to separate KNO$_3$ and to destroy residual NDMA.

Methylene chloride and NDMA may then be separated in a flash evaporator. Recovered methylene chloride my be recycled to a holding tank and returned to the feed of the extraction column. Thus, small amounts of water and NDMA may be carried over as an azeotrope need not be lost but may be recycled through the extraction column. The NDMA may then be concentrated to 99.5% and transferred to a holding tank for the hydrogenation step.

The extraction separates organics soluble in methylene chloride but rejects inorganic salts. Therefore, all the KNO$_3$ will be separated from methylene chloride and be available for the recovery of potassium nitrate salt as a solid by-product. While traces of NDMA will intially be present in this potassium nitrate by-product, a significant object of this invention includes even the successful removal of this source of NDMA pollution by a high temperature melt on the potassium nitrate by-product. A major by-product of nitrosation, N-nitrodimethylamine (dimethylnitramine), is also concentrated by the extraction process. As the nitramine can be reduced to UDMH, this does not represent a yield loss. Minor amounts of other derivatives can be detected in small (less than 0.1%) amounts but do not interfere with the hydrogenation.

These minor impurities apparently carry through the hydrogenation and are concentrated in the distillation step. Should these materials begin to contribute out-of-specification material, a purge stream of some 5-10% of the reboiler bottoms will control these products at a satisfactory level.

It should be emphasized that the extraction step taught herein allows for a thermal destruction of liquid wastes comprising only organic compounds including those nitrosamines such as NDMA, thus avoiding any liquid waste combination of inorganic salts with organic compounds which would result from inorganic salts. It is well known that in liquid form inorganic salts, such as KNO$_3$, would destructively react even with a glass liner in a thermal destruction apparatus.

After extraction, the instant process requires a hydrogenation which is followed by distillation. As such, hydrogenation is the only effective known way to convert NDMA into a reasonable yield of UDMH. U.S. Pat. No. 3,102,887 by Thatcher, a coinventor herein, illustrates this hydrogenation reaction per se and the type of catalytic hydrogenation employed within the instant process is not critically dependent on the form of catalyst employed.

While the extraction step constitutes a preferred step in the illustrative embodiment of the present process, it should be noted that the UDMH may also be successfully produced by consecutive nitrosation, hydrogenation and distillation reactions, as hereinbefore indicated.

For example, an early process successfully hydrogenated an approximately 35% aqueous solution of NDMA in the presence of KNO$_3$ using a 5% Pd/C catalyst. This hydrogenation led to the formation of excess NH$_3$ by reduction of KNO$_3$ producing a strongly basic solution through the formation of KOH.

In addition, early distillations were successfully carried on without isolation of the catalyst. Laboratory distillation studies suggested that the catalyst promoted some decomposition of UDMH and catalyst which had undergone a distillation process could not be economically regenerated for recycle.

As the procedures for nitrosation developed, the hydrogenation catalysts were chosen simply on the following criteria:
1. Percent conversion to UDMH with a minimum of side reactions that form undesirable by-products.
2. Lowest concentration to a possible elimination of NDMA during the reaction to eliminate or minimize problems of disposing of unreacted NDMA in the process effluents.
3. Speed of reaction.
4. Recyclability of catalyst.
5. Cost.
6. Availability.

Effective catalysts for the process herein are, for example, those comprising a 5% palladium deposited on carbon, and rhodium depositions have also been found useful.

According to the preferred embodiment a nitrate, or KNO$_3$, free NDMA solution may be first concentrated prior to the hydrogenation step. This prior concentration can be effected sequentially be an extraction of NDMA from the salt solution with methylene chloride; distillation of methylene chloride until the solution is approximately 90% NDMA; and addition of water to the desired NDMA concentration level.

This extraction and concentration before hydrogenation is efficient because it provides nearly complete recovery of the NDMA from the salt solution and has the added advantage of permitting almost infinite control of the final NDMA concentration.

Hydrogenation without nitrate allows a somewhat improved effectiveness as evidenced by yields, consistency and selectivity. Average conversion of NDMA to UDMH was 67.69 weight percent as compared to 63.09 weight percent with nitrate in the solution. In addition, about ⅓ less time was required to reach a 0% NDMA level and about ½ as much hydrogen input. Some reduction in hydrogen usage was expected since the combination of hydrogen and nitrate salt, under the experimental conditions, results in some ammonia generation. As a result the ammonia level of the final sample was five times less without the nitrate. A reduced ammonia level in the final product is advantageous as it would reduce product distillation problems and facilitate catalyst recycle.

After hydrogenation the final UDMH product is first distilled. As has been indicated this last major step in producing the UDMA according to this invention has been successfully carried out as the third consecutive step in the same reactor as the nitrosation and hydrogenation steps.

A typical distillation from such a run was as follows:

After the hydrogenation reactor was purged of hydrogen, the distillation was started at approximately 170° F for a DMA/light ends cut. At approximately 190° F reactor temperature the intermediate cut on DMA/UDMH was attempted. Difficulty in separating UDMH/H$_2$0 was encountered. Finally, after several low volume cuts, DMA was reduced to below four area percent by gas chromatographic analysis. The reactor temperature was now 233° F at 10 psig. Column temperatures were running high due to water carry over. UDMH purification was attempted by increasing the reflux ratio to control column temperatures, however, water misibility proved to be a problem. Nonetheless an average area percent of distillate contained 60% UDMH and 35% water with 86% UDMH-10% water as a best effort.

During this time, laboratory distillations designed to determine material balances and theoretical plate requirements for a still had determined that diethanolamine (DEA) was a suitable replacement for NaOH in the separation of UDMH from NDMA. The mechanism of action differs from that of strong caustics since in the DEA system there is no phase separation evident. Concentrations of up to 300 percent DEA with UDMH samples were made without apparent phase separation.

It should be noted that the instant process specifically teaches DEA, and equivalent organic bases, and as such is a significant improvement per se over the prior art attempts at distillation of UDMH. For example the prior art conventionally has used sodium hydroxide as an input, as illustrated by U.S. Pat. No. 2,858,254. With organic distillation bases such as DEA, (and also including morpholine, diethylaminoethanol and dimethylaminoethanol) there will be no attacking of the glass in a thermal destructor. For example, at the fifth cut of the distillation (as hereinafter illustrated in the preferred embodiment at FIG. 2.) there will be no inorganic salt present within the liquid effluent containing the organic salt NDMA which is sent to a thermal destructor. Therefore, a major object of the invention, to wit, thermal destruction of NDMA in waste streams will be physically possible. The following illustration of the preferred embodiment of the process is best illustrated with reference to the enclosed drawings which illustrate the process flows from the individual reaction steps. The description of the preferred embodiment is understood to be illustrative only and not limitive of the invention in any manner. The illustration of the process according to the instant invention is primarily illustrated with reference to these drawing figures as further amplified by the following comments which are by way of amplification of the essential processes illustrated in the drawings.

DESCRIPTION OF THE PREFERRED PROCESS:

FIG. 1 similarly illustrates the extracted $KNO_3$ solution going to a salt recovery system.

Figure 2:
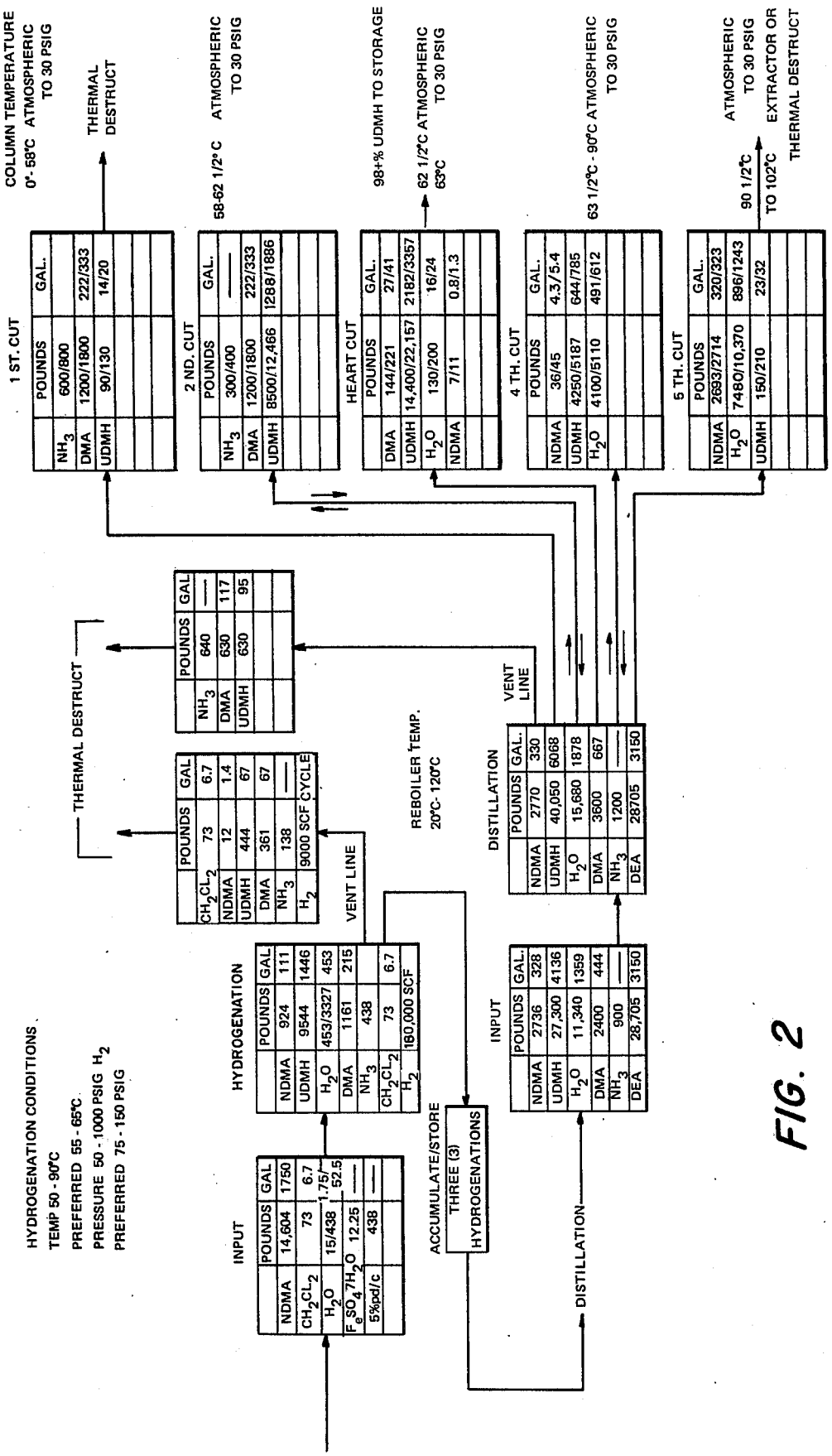
FIG. 2 is a continuation of FIG. 1 for the specific process steps of hydrogenation of the NDMA from FIG. 1 together with the subsequent distillation step with further illustration of recycling and vents to a thermal destruct step.
Figure 6:
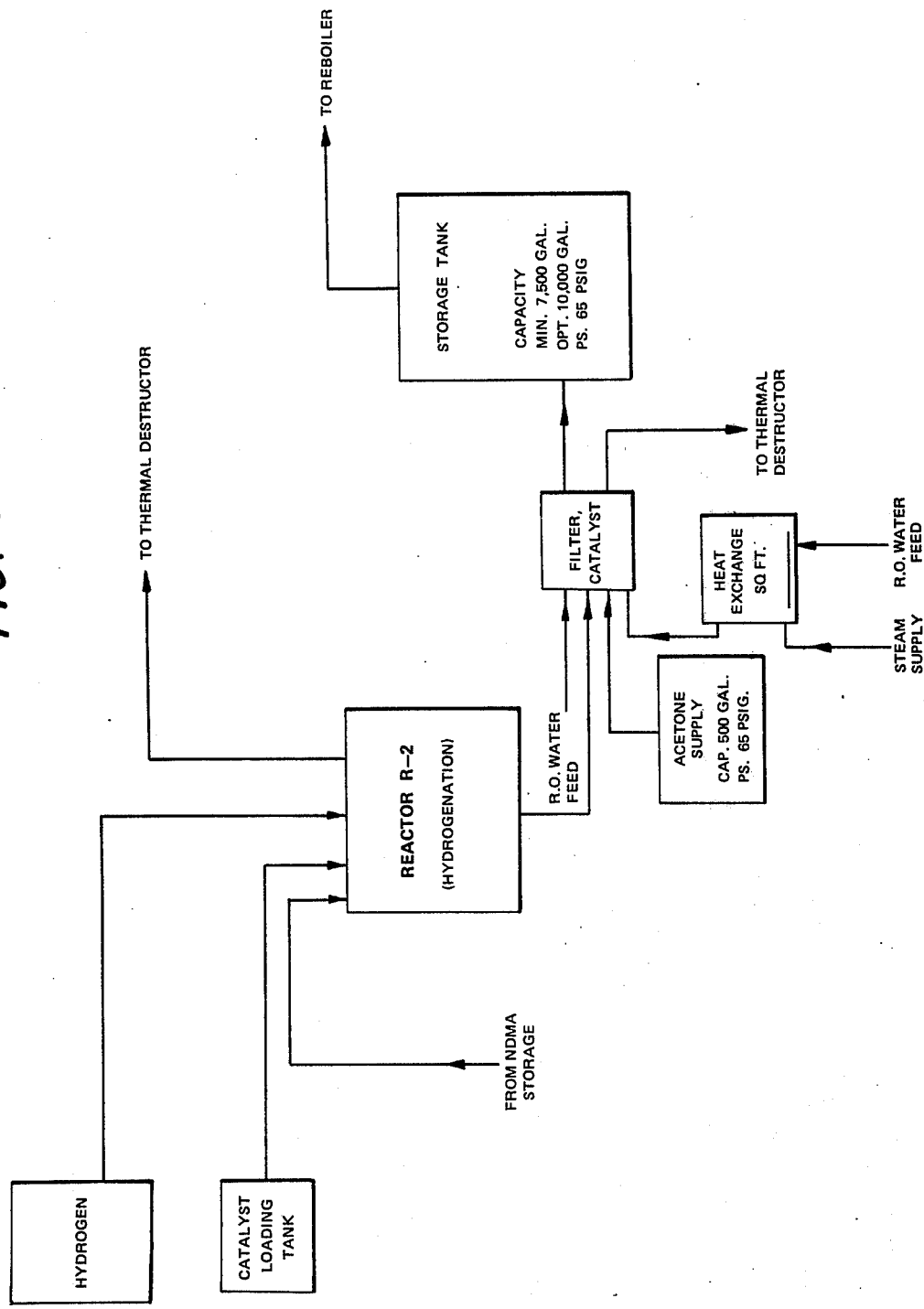

FIG. 6 schematically illustrates an apparatus operable for the hydrogenation and catalyst washing process as represented in FIG. 2.

Figure 3:
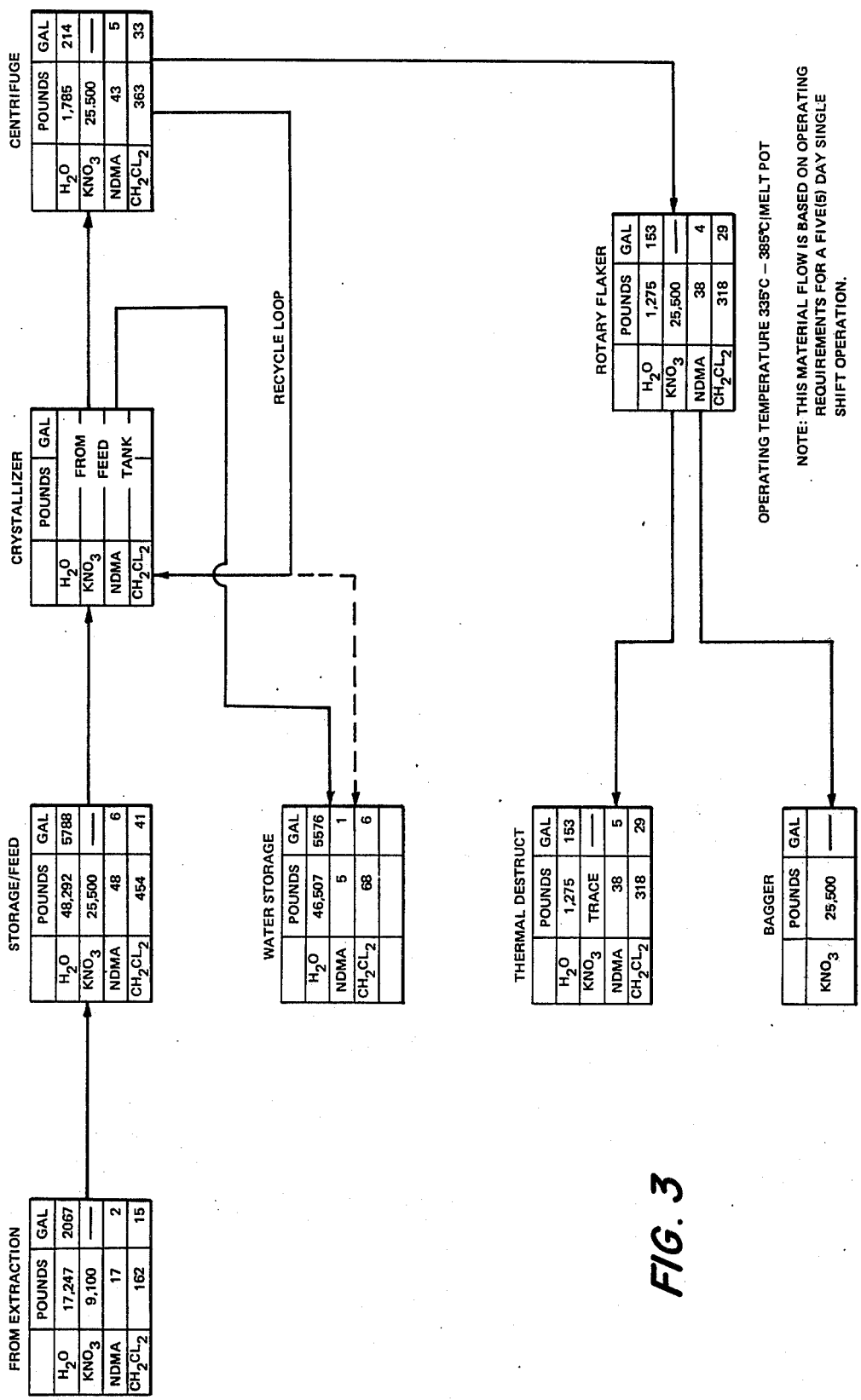
FIG. 3 is a material flow of the $KNO_3$ salt solution from the extraction process of FIG. 1 together with a material flow illustration to the ultimate production of the solid by-product $KNO_3$.
Figure 7:
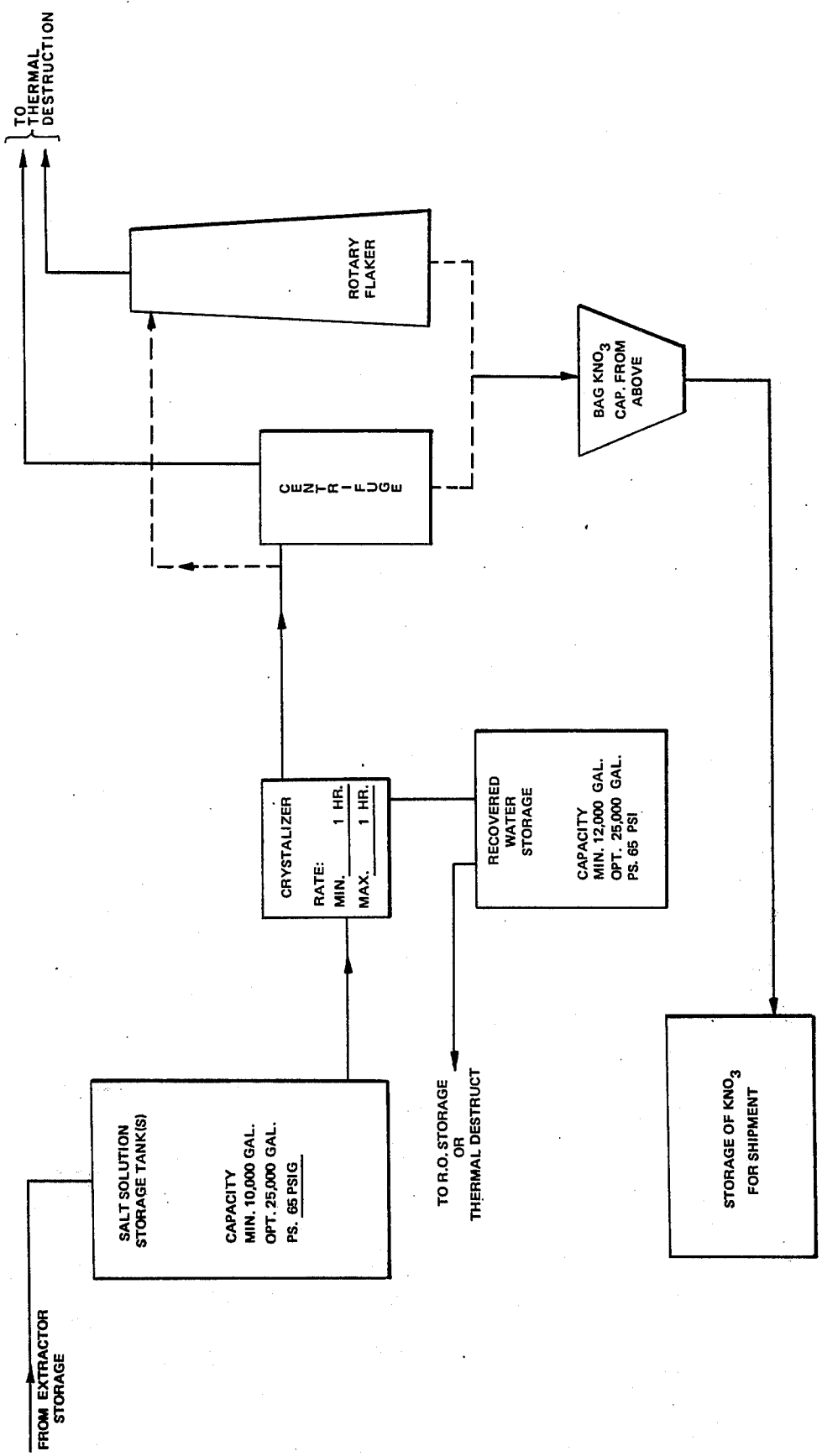

FIG. 7 schematically illustrates a process operable to perform the salt treatment step of the process as illustrated in FIG. 3.

Figure 1:
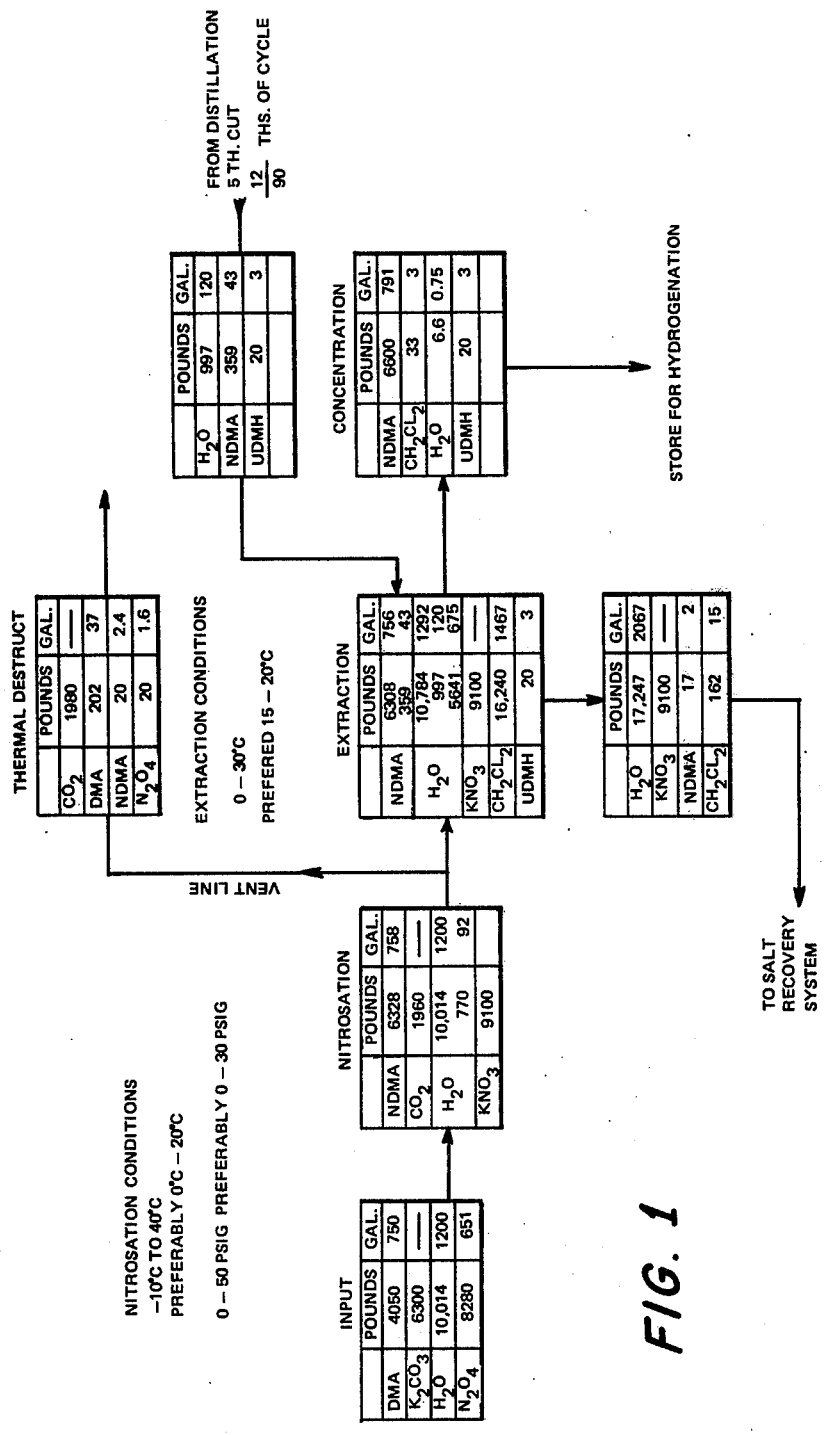
FIG. 1 illustrates the material flows from a nitrosation and through extraction and concentration of the NDMA previous to hydrogenation.
Figure 5:
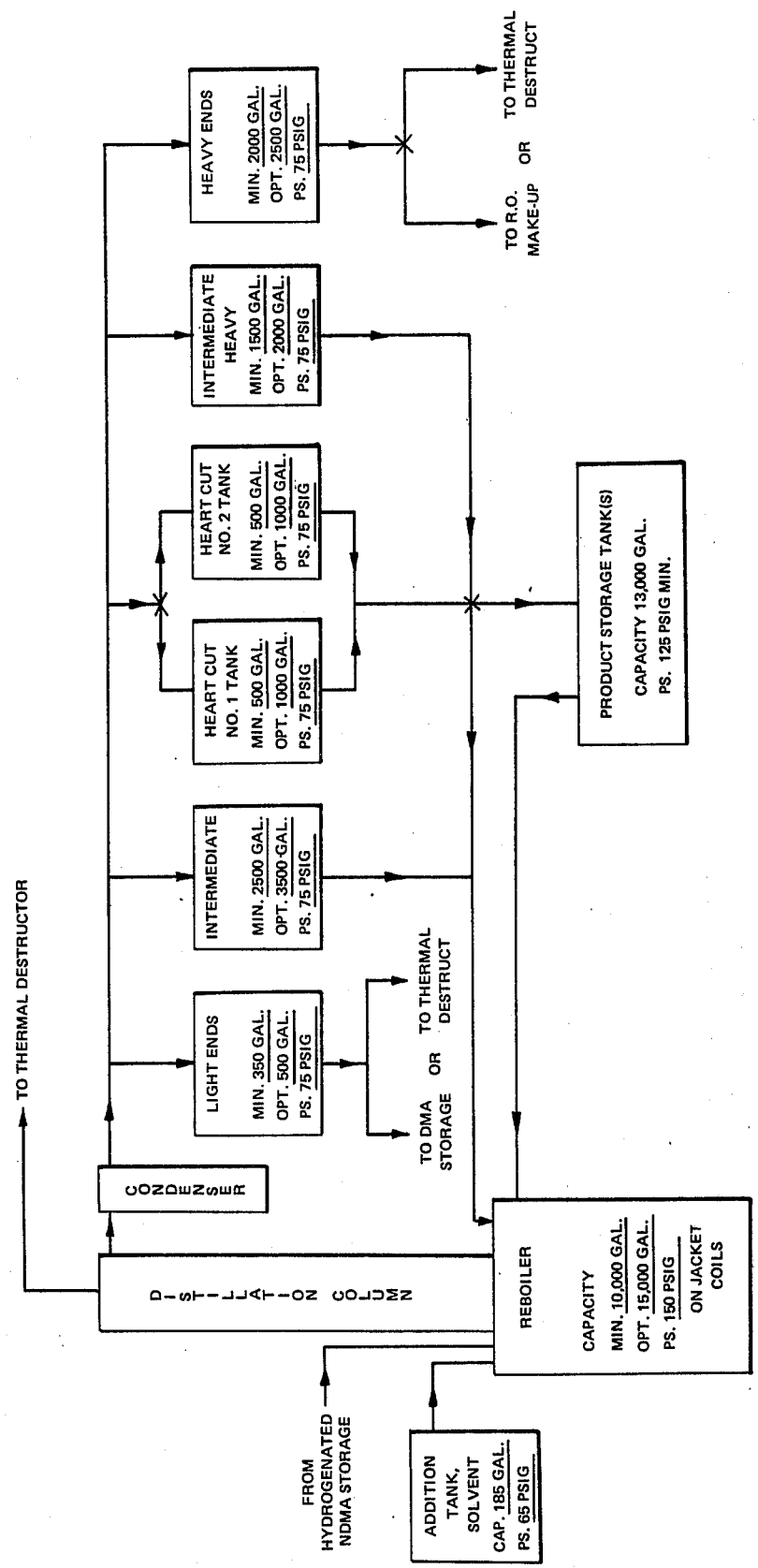
FIG. 5 illustrates an aparatus operable for the distillation step as illustrated in the material flow of FIG. 2.

As can be seen from the consideration of the overall process as represented most clearly by FIGS. 1-3, the entire process provides for disposal of all non-recyclable waste products through a thermal destructor thus allowing for manufacture of UDMH as an entire closed loop system. From this process there is a primary UDMH product resulting from the distillation, as primarily recovered after recycling from the heart cut of the distillation step as shown in FIG. 2 and 5.

The other essential output of the process according to the instant invention is the by-product of NDMA free potassium nitrate as recovered in the salt recovery illustrated in FIGS. 3 and 7.

As has been discussed, it is the primary achievement of the process according to the instant invention that the production of UDMH as taught herein is without release of NDMA into the atmosphere through any waste streams. A further distinct advantage of the process according to the instant invention results from the particular extraction step which synergistically operates within the total process to allow for the separation of $KNO_3$ in a NDMA-free form. As can be seen from a consideration of the process according to this preferred embodiment, all NDMA waste streams are either recycled through the process or sent as a vapor phase to a thermal oxidizer. It should be emphasized that NDMA is in all cases thermally destroyed while in the vapor state. As has been explained, any attempt for thermal destruction of a liquid combination of inorganic salts with organic compounds which would result from inorganic salts will destructively react with even a glass liner in any thermal destruction apparatus. Therefore, it is primary object of this invention to avoid the necessity for destroying in liquid from any inorganic salts such as $KNO_3$. Rather, a particular advantage of the instant process involves the recycling of all aqueous streams with an eventual thermal destruct of the hazardous NDMA as a vapor with the advantageous by-product of solid $KNO_3$.

As illustrated in FIG. 1 the nitrosation reaction is a conventional matter of converting DMA into NDMA. It should be noted that the essential aspect of this process does not necessarily require the initial step of nitrosation but rather could proceed from the products of the nitrosation reaction as illustrated at FIG. 1. However, because the only parctical manner of producing NDMA is from a direct nitrosation the preferred embodiment shows the respective amounts of reactants necessary for a direct input in illustration of the instant inventive process. While nitrosation is a well known manner of producing the NDMA starting material, it should be noted that the instant preferred nitrosation employs dinitrogen tetroxide ($N_2O_4$).

As shown, the nitrosation step is performed in a reactor which as illustrated would be on the order of 3,000 gallons with each batch having the formulation depicted on FIG. 1. As shown from the initial reactants a yield of 6,328 pounds of NDMA will be produced, in addition 770 pounds of water will have been generated in addition to the 10,014 pounds of water from the initial input. Significantly, 1,980 pounds of carbon dioxide ($CO_2$) will have been manufactured during the nitrosation reaction. This large amount of $CO_2$ must therefore be vented during its generation to keep reactant pressures within operating requirements. With this venting a nitrogen atmosphere is introduced into the nitrosation reactor vessel and as a result the vent line illustrated in FIG. 1 would carry off certain small amount of NDMA in the vapor state, the vapor state resulting from the vapor pressure of the NDMA within the reactor vessel during the nitrogen purge. Similarly, the vapor purging carries off 202 pounds of DMA and 20 pounds of dinitrogen tetroxide. At this point it should be noted that this vent line goes to a thermal destructor and the 20 pounds of NDMA in the vapor state in an organic salt with no inorganic salts present ina liquid state and therfore the thermal destruction illustrated in FIG. 1 is accomplished without the danger of inorganic salt oxidation of a glass thermal destructor vessel. The main product stream from the nitrosation reaction is illustrated as an input to the extraction step with the respective amounts of reactants in the extraction illustrated by the boxed amounts as the upper number with the subsequent numbers illustrating the amounts of reactants which are supplied from the various recycle positions. Since development of this new process has confirmed the desirability of hydrogenating concentrated NDMA, it is preferred at this point to remove the NDMA from the nitrosated reaction. Therefore, the extraction step as illustrated is performed in an extraction column using methylene chloride ($CH_2Cl_2$) as an extractive solvent. During this extraction step and to ensure proper extraction column operation the liquid potassium nitrate ($KNO_3$) must remain in agueous solution during extraction. This is assured by adding 5,641 pounds of water which is recycled from the salt recovery plant as shown in FIG. 3 and 997 pounds of water returned from the fifth cut distillation cycle as shown in FIG. 2. At this point the fifth cut of the distillation cycle will also contain specified quantities of NDMA and UDMH. If the fifth cut from the distillation cycle is preferably not recycled herein, but rather sent to a thermal destructor, as illustrated in FIG. 2 the thermal destruction of this fifth cut distillation may similarly be easily accomplished because there are no liquid constituents of inorganic salts from the extraction operation. In this sense the use of methylene chloride as the extracting solvent instead of the prior art approach of sodium hydroxide allows both for a by-product extraction of $KNO_3$ without sodium hydroxide and a vapor formed from the fifth cut of the distillation that similarly is not plagued by inorganic salts. It should be noted that the use of methylene chloride or equivalent organic bases both enables the recovery of potassium nitrate and allows for the respective thermal destructions according to the instant process. If the fifth cut from the distillation is to be sent to a thermal destructor, then additional make-up water for the extraction process may be obtained from the salt recovery process. The extraction process is designed to remove the $NDMA/CH_2CL_2$ from the $KNO_3$ water so that the NDMA solution may then be fed to a concentrator with the $KNO_3$ water fed as a by-product to the salt recovery system. While specific quantities of other chemicals are respectively separated at this point, the process herein allows for successful removal of NDMA both from the UDMH product and the by-product salt.

During the subsequent concentration step as illustrated in FIG. 1, the methylene chloride will be removed from the NDMA to approximately 0.5% and the water content will be reduced to approximately 0.1%. The methylene chloride water will be recovered and stored in the extractor feed tank for reuse on a subsequent extraction cycle. The thusly concentrated NDMA may then be placed in a storage holding tank for the hydrogenation step. With the exemplary reactants as illustrated in FIGS. 1-4 approximately three nitrosations will be required to supply the NDMA illustrated for one hydrogenation.

Figure 4:
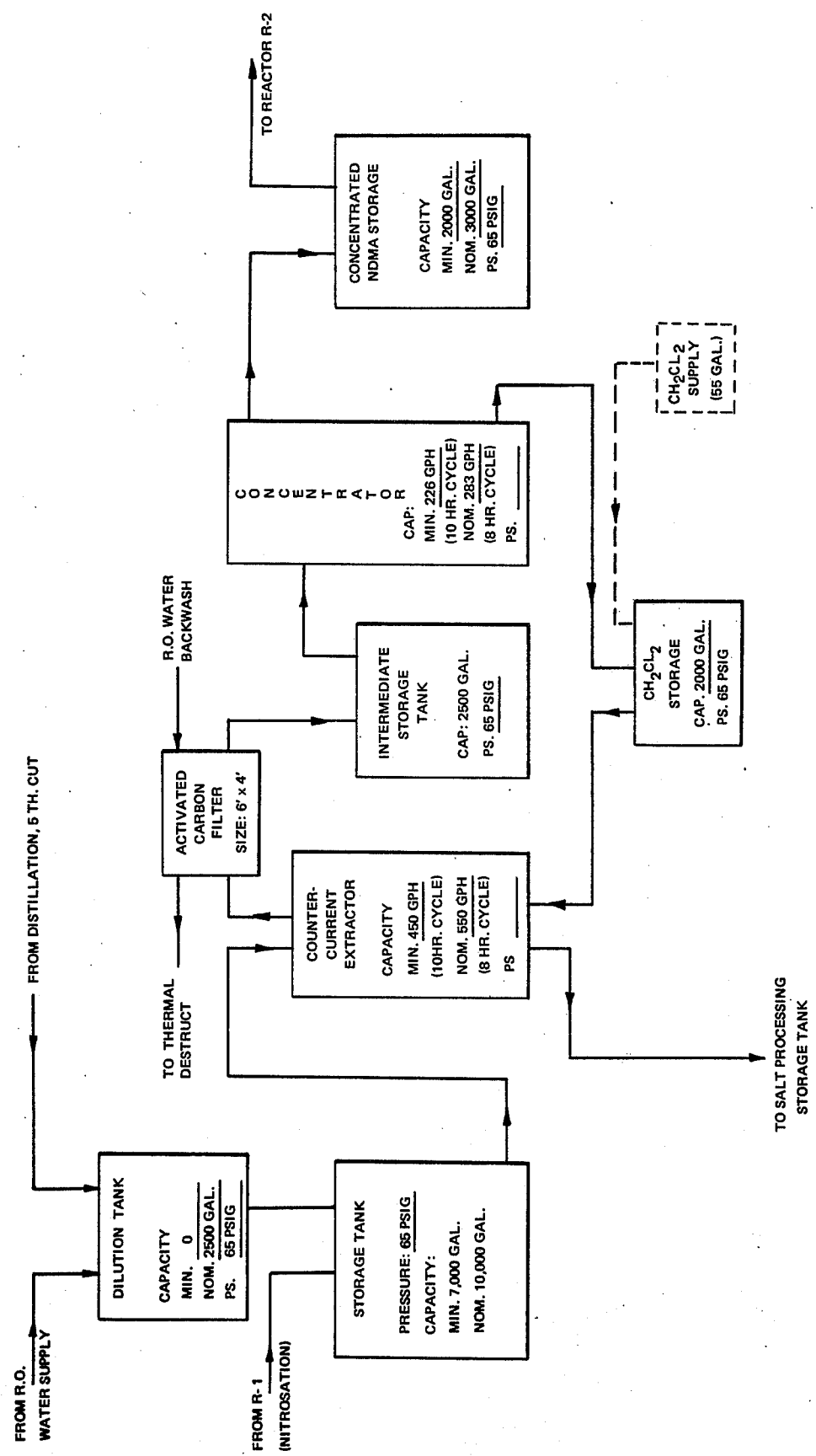
FIG. 4 illustrates a preferred apparatus for the process taught herein, specifically the extraction and concentration of NDMA.

The operating parameters for the nitrosation reaction are well known, with the range of temperatures and pressures represented by the aforementioned Reilly patent, U.S. Pat. No. 3,153,094. As shown in FIG. 1, the general operating range of temperature and pressure are as indicated at the steps along the material flow lines. Similarly, FIG. 4 represents operating parameters for an exemplary apparatus for performing the method steps of extraction and concentration according to the instant invention. If a counter-current extraction is used for this extraction step, the sizing of the column required can be determined by considering several constants. By laboratory tests a distribution coefficient (m) of NDMA between methylene chloride and water can be determined. From this the required number of theoretical plates for extraction may be calculated. Thus, the theoretical plate calculation may be as follows:

1) From laboratory studies the distribution coefficient (m) for NDMA between methylene chloride and water is 3.5.
2) Starting pounds NDMA/pound aqueous phase
$(X_f) = \frac{6667}{26522}$
$= 0.2514$ lb/lb.
3) With the requirement of <0.1% NDMA in aqueous discharge
$(X_n)$, $X_n = \frac{26.522}{26522}$ or 0.0010 lb/lb.
4) Ratio $\frac{X_n}{X_f} = \frac{0.0010}{0.2514} = 0.0040$ fraction unextracted
5) The extractor factor $= \frac{\text{lbs. methylene chloride}}{\text{lbs. aqueous phase}} \times (m)$
$= \frac{\text{lbs. methylene chloride}}{26522} \times 3.5$ With E and fraction unextracted determined, the number of theoretical plates can be determined graphically from manufacturer's data.

| Lbs $CH_2Cl_2$ | E | Theoretical Plates (Graphical Solution) | Combine Flow 10 Hr Cycle | Rates Gal/Hr 8 Hr Cycle |
|---|---|---|---|---|
| 16,240 | 2.14 | 5.8 | 453 | 567 |
| 20,000 | 2.63 | 5.2 | 487 | 609 |
| 24,000 | 3.16 | 4.5 | 523 | 654 |

The hydrogenation and distillation steps according to the instant process can be best appreciated by reference to FIGS. 2 together with the further apparatus illustration and operating parameters of FIG. 4 and FIG. 5 Additionally, FIG. 6 illustrates a further advantageous catalyst wash step which allows for reuse of the catalyst after the hydrogenation step.

The hydrogenation input shows that the methylene chloride is carried along in the aqueous NDMA stream and according to this preferred embodiment there is shown the addition of an iron promoter together with an illustated catalyst of 5% paladium deposited upon carbon. As shown most clearly in FIG. 2 the hydrogenate includes for this illustrative embodiment of the inventive process 9,544 pounds of UDMH. The hydrogenation may be performed in a separate 3,000 gallon closed reactor as illustrated. This reactor is shown to be charged with 14,604 pounds of 99.5% NDMA as accumulated from the extraction/concentration cycles. The reactors are then purged with nitrogen to displace the air and then with hydrogen to displace the nitrogen preparatory to the actual hydrogenation step. It is significant that all purges of the reactor are vented to the thermal destruct as shown which again allows for disposal of vaporized organics, mostly NDMA without the destructive effect that inorganic salts such as $KNO_3$ would have upon a thermal destructor's glass liner. The operating parameters for the hydrogenation are of course well known and the general parameters are illustrated in the previously mentioned Thatcher patent, U.S. Pat. No. 3,102,887. Additionally, the known step of hydrogenation is illustrated in Great Britain Pat. No. 797,483. For purposes of this process the general operating parameters are as illustrated in FIG. 2 and FIG. 6.

After hydrogenation, the reactor is vented to reduce the hydrogen pressure to atmospheric pressure and then the hydrogen atmosphere is displaced by purging with nitrogen. These hydrogen vents and nitrogen purges are again fed to the thermal destructor. These streams will contain a significant amount of $NH_3$, DMA and UDMH because of their low boiling points. As further illustrated in FIG. 6 an advantageous operation of this process also allows for removal of the catalyst after each hydrogenation run by filtration through a plate and frame filter using nitrogen pressure in the reactor for the motive power. When the filtration of the catalyst is complete the filtrate is held for distillation. The catalyst is then cleaned for reuse of recovery with steam and acetone washes. As shown in FIG. 6 these wash streams are sent to the thermal destructor for disposition.

Three hydrogen filtrates are advantageously accumulated as illustrated in FIG. 2, in order to make up one distillation charge according to this preferred process example. In addition, intermediate distillation cuts from a previous distillation run may be advantageously recycled to the reboiler at appropriate times in the distillation. The initial phase of the distillation is above atmospheric pressure so as to improve separation of the light end cuts. This excess pressure of nitrogen and light end cuts are shown to be bled to the thermal destructor in order to effect a complete destruction of all organics. While five cuts including a middle heart cut are illustrated in FIG. 2 and further represented in FIG. 5, it should be noted that DMA distills anywhere from 12° C to 60° C. The exemplary percentage of UDMH in the heart cut as illustrated in FIGS. 2 and 5 is controlled mainly by the associated NDMA content. As shown in FIG. 5 and as developed according to the flows of FIG. 2 with a reflux distillation ratio of 6/1, UDMH of greater than 99.5% can be recovered as a heart cut. The NDMA content during the distillation in turn closely parallels the $H_2O$ content of the heart cut. When the NDMA exceeds the desired concentration, intermediate high boiling fractions still contain a significant amount of UDMH and will be returned to the distillation still with the next distillation in plant operation. It should be noted that the organic base DEA is not a problem during this distillation step because it has no odor, it is not volatile and also has a high boiling point- -above 187° C. Pure DEA has a high freezing point (28° C), so at room temperature DEA is a solid. In order to reconstitue DEA for subsequent use, a specific quantity of water, less than 5%, will remain in the DEA to prevent freezing. Is has been found that essentially 100% recovery of DEA may be had from this distillation step.

As has been described, the fifth cut may either be recycled to the extractor or sent to a thermal destruct. Once again this vapor contains NDMA without the presence of inorganic salts which would preclude the use of a thermal destruction step to conveniently dispose of the organic salt NDMA. As has been noted, while DEA is illustrated in the preferred embodiment as the organic base input into the distillation step, it has been found that morpholine, dimethylaminoethanol and diethylaminoethanol are similarly useful for the organic base in this distillation step.

As has been explained and illustrated, the primary function of this process is the creation of UDMH which results from the heart cuts in this distillation step. However, a primary advantage of this operation is the unexpected result that a solid by-product may be purified of NDMA contamination and realizable as a valuable by-product of the overall process. The potassium nitrate recovery system is specifically illustrated in the process at FIG. 3 and as such constitutes an unexpected advantage of the basic processes taught herein. An aqueous salt phase from the NDMA extraction as shown in FIG. 1 comprises the input to the salt recovery subprocess of FIG. 3. As illustrated in FIG. 3 taken together with the exemplary apparatus and operating parameters of FIG. 7, the accumulated $KNO_3$ solution containing small amounts of NDMA is stored to constitute a feed into a crystallizer. A crystallizer simply functions to initially separate the water and the salt, the water transferred to holding tanks preparatory to a use as a make-up water for the earlier nitrosation reaction. Crystallizers per se are well known and the only requirement of this method step is that the excess water be recyclable back to the water storage for reuse. It should be noted that traces of NDMA and methylene chloride are also illustrated to be carried back to this water storage pump. As such this aqueous recycle stream as shown in FIG. 3 includes only 5 pounds of NDMA and because it is recycled there is no danger of loss of this NDMA into the immediate environment. From the crystallizer the slurry of $KNO_3$ is further fed to a conventional centrifuge to further remove water and produce crystalline $KNO_3$ of approximately 7% moisture content. This product from the centrifuge is then fed to an enclosed melt pot on a rotary flaker. As such rotary flakers are well known and the melt pot in the flaker serves two purposes at above 300° C, it reduces the $KNO_3$ cake to an ultimate salt purity and more importantly decomposes any remaining NDMA. In this rotary flaker the melt is maintained at 385° C for a long enough period to ensure total destruction of NDMA. Experiments have shown that 30 minutes at 385° C has resulted in no trace of NDMA being found in the potassium nitrate. As shown in FIG. 3 the resultant final by-product is $KNO_3$ in the amount of 25,500 pounds which is equal to the orginal feed batch amount. As such, the potassium nitrate salt thus produced meets military specifications and therefore has application in pyrotechnics and black powder, gun and rocket propellants and as a special additive for related uses.

With respect to the thermal destructor which in all cases destroys any vaporized NDMA from various points in this process as previously discussed, such thermal destructors are readily available. The thermal destructors employable according to this process are designed to incinerate liquid and gaseous organic-aqueous waste. Such a thermal destructor is one made by the John Zink Company. Within this thermal combustion, a combustion air fan supplies reaction air and the reducing section produces a high temperature environment in which the NOx from the waste stream preliminarily combusts to give $N_2$, $O_2$ and $H_2O$. With a subsequent quench using inert water to prevent secondary NOx formation during final combustion, the excess combustibles will be oxidized at near stoichmetric conditions. The combustion products are then vented to the atmosphere without introducing any NDMA thereto.

Having disclosed a preferred process according to this invention, it is understood that many variations to the process can be made without departing from the basic concept taught herein. We intend, therefore, to be limited only in accordance with the appended claims.

We claim:

1. A process for preparing unsymmetrical dimethylhydrazine by the catalytic hydrogenation of N-nitrosodimethylamine and recovering potassium nitrate as a by-product consisting essentially of the steps of:
   A. nitrosating an aqueous solution of dimethylamine by reaction with dinitrogen tetraoxide and potassium carbonate at a pressure from atomospheric to 50 psi g and a temperature from $-10°$ C to $40°$ C to produce an aqueous solution of N-nitrosodimethylamine and potassium nitrate and gaseous carbon dioxide; and,
   B. extracting all of said potassium nitrate from said aqueous solution by a liquid extraction at a temperature between $0°$ C to $30°$ C wherein methylene chloride is added as an extractive solvent to said aqueous solution, and withdrawing an aqueous solution of said potassium nitrate and a separate potassium nitrate-free stream of N-nitrosodimethylamine in solution with methylene chloride; and,
   C. hydrogenating the potassium nitrate-free stream of N-nitrosodimethylamine solution in the presence of a hydrogenation catalyst by reacting said stream with hydrogen at a pressure from 50–1000 psi g and at a temperature from $50°$–$90°$ C to produce an aqueous product solution containing unsymmetrical dimethylhydrazine; and
   D. distilling said product solution in the presence of an organic distillation base selected from the group consisting of diethanolamine, morpholine, diethylaminoethanol and dimethylamino ethanol, and taking off unsymmetrical dimethylhydrazine as a heart cut substantially free of water, N-nitrosodimethylamine, and said distillation base.

2. The process according to claim 1 wherein said withdrawn aqueous solution of potassium nitrate includes trace elements of N-nitrosodimethylamine and said potassium nitrate is substantially separated out from said aqueous solution and thereafter melted at a temperature above $300°$ C for a time sufficient to vaporize all remaining water and trace elements of N-nitrosodimethylamine, removing solid potassium nitrate as a by-product and venting all vaporized products to a thermal destructor wherein said vaporized N-nitrosodimethylamine is oxidized and thermally destroyed.

3. A process according to claim 2 wherein said step of substantially separating said potassium nitrate out from solution includes crystallizing the potassium nitrate to a slurry and recycling water containing trace element of N-nitrosodimethylamine and methylene chloride as make-up for said nitrosation step, and centrifuging said potassium nitrate slurry to further remove water and produce crystalline potassium nitrate of approximately 7 percent moisture content for said melting step.

4. A process according to claim 3 wherein the step of melting said potassium nitrate including trace elements of N-nitrosodimethylamine is at a temperature from $335°$ C to $385°$ C.

5. A process according to claim 1 wherein said withdrawn potassium nitrate-free stream of N-nitrosodimethylamine in solution with methylene chloride is concentrated until said stream is approximately 90 percent, by weight, N-nitrosodimethylamine by evaporating off and recycling methylene chloride to said extraction step, and said concentrated stream is supplied to said hydrogenation step.

6. A process according to claim 1 wherein said gaseous carbon dioxide produced during said nitrosation step includes small amounts of N-nitrosodimethylamine in the vapor state, and said vapors are vented to a thermal destructor wherein said vaporized N-nitrosodimethylamine is oxidized and thermally destroyed.

7. A process according to claim 2 wherein said extraction step is a counter-current liquid extraction wherein said potassium nitrate is maintained in aqueous solution by recycling water from said step of sybstantially separating potassium nitrate from its aqueous solution.

8. A process according to claim 1 wherein said distillation step is carried out in a distillstion column maintained at from atmosphereic to 30 psi g wherein a light end cut containing N-nitrosodimethylamine in the vapor state is bled at column temperatures between $0°$ C and $58°$ C and sent to a thermal destructor wherein it is oxidized and thermally destroyed.

9. A process according to claim 8 wherein said heart cut is taken off at column temperatures of $62.5°$ C to $63°$ C and said organic distillation base selected is diethanolamine.

10. A process according to claim 8 wherein a heavy end cut containing water and N-nitrosodimethylamine in the vapor state is bled at column state is bled at column temperatures between $90.5°$ C and $102°$ C and is sent to said extracting step as a recycle stream.

11. A process according to claim 8 wherein a heavy end cut containing N-nitrosodimethylamine in the vapor state is bled at column temperatures be between $90.5°$ C and $102°$ C and is sent to a thermal destructor wherein it is oxidized and thermally destroyed.

12. A process according to claim 1 wherein said hydrogenation step further inclues venting all remaining gaseous products and vapors containing N-nitrosodimethylamine to a thermal destructor wherein said vaporized N-nitrosodimethylamine is oxidized and thermally destroyed.

13. A process for preparing unsymmetrical dimethylhydrazine by the catalytic hydrogenation of N-nitrosodimethylamine which initially is in an aqueous solution with potassium nitrate, wherein crystalline potassium nitrate is recovered as a by-product, said process consisting essentially of:
   A. extracting all of said potassium nitrate from said initial aqueous solution by a liquid extraction at a temperature between $0°$ C to $30°$ C wherein methylene chloride is added as an extractive solvent to said initial aqueous solution and withdrawing an aqueous solution of said potassium nitrate and a separate solution of N-nitrosodimethylamine in solution with methylene chloride; and
   B. hydrogenation the potassium nitrate-free stream of N-nitrosodimethylamine solution in the presence of a hydrogenation catalyst by reacting said stream with hydrogen at a pressure from 50 to 1000 psi g and at a temperature from $50°$ C to $90°$ C to produce an aqueous product solution containing unsymmetrical dimethylhydrazine, and;

C. distilling said product solution in the presence of an organic distillation base selected from the group consisting of diethanolamine, morpholine, diethylaminoethanol and dimethylaminoethanol, and taking off unsymmetrical dimethylhydrazine as a heart cut substantially free of water, N-nitrosodimethylamine and said organic distillation base, and;

D. recovering crystalline potassium nitrate from said withdrawn aqueous solution which also includes trace elements of N-nitrosodimethylamine by substantially separating out the water to create a slurry at a temperature above 300° C for a time sufficient to vaporize all water and trace elements of N-nitrosodimethylamine remaining in said slurry, and removing solid potassium nitrate as a by-product and venting all vaporized products to a thermal destructor wherein said vaporized N-nitrosodimethylamine is oxidized and thermally destroyed.

* * * * *